(12) United States Patent
Chen et al.

(10) Patent No.: US 11,839,416 B2
(45) Date of Patent: Dec. 12, 2023

(54) SURGICAL EXPANDABLE IMPLANT

(71) Applicant: POINT ROBOTICS (SINGAPORE) PTE. LTD., Singapore (SG)

(72) Inventors: Chih-Wei Chen, Hsinchu (TW); Hao-Kai Chou, Hsinchu (TW); Xiu-Yun Xiao, Hsinchu (TW)

(73) Assignee: POINT ROBOTICS (SINGAPORE) PTE. LTD., Singapore (SG)

( * ) Notice: Subject to any disclaimer, the term of this patent is extended or adjusted under 35 U.S.C. 154(b) by 429 days.

(21) Appl. No.: 17/138,935

(22) Filed: Dec. 31, 2020

(65) Prior Publication Data

US 2022/0202459 A1 Jun. 30, 2022

(51) Int. Cl.
| | | |
|---|---|---|
| *A61B 17/86* | (2006.01) | |
| *A61B 17/70* | (2006.01) | |
| *A61B 17/88* | (2006.01) | |
| *A61B 17/84* | (2006.01) | |
| *A61B 17/74* | (2006.01) | |

(52) U.S. Cl.
CPC ........ *A61B 17/864* (2013.01); *A61B 17/7082* (2013.01); *A61B 17/7098* (2013.01); *A61B 17/8805* (2013.01); *A61B 17/7019* (2013.01); *A61B 17/744* (2013.01); *A61B 17/844* (2013.01); *A61B 17/8625* (2013.01); *A61B 17/8685* (2013.01); *A61B 17/8858* (2013.01); *A61B 2017/8655* (2013.01)

(58) Field of Classification Search
CPC ..... A61B 17/56; A61B 17/68; A61B 17/7001; A61B 17/7019; A61B 17/7074; A61B 17/84; A61B 17/842; A61B 17/844; A61B 17/8625; A61B 17/8685; A61B 17/8858; A61B 17/744; A61B 2017/8655; A61F 2/442; A61F 2/4405; A61F 2/4455
USPC ................ 606/300, 304, 308–310, 313, 320, 606/326–327, 328
See application file for complete search history.

(56) References Cited

U.S. PATENT DOCUMENTS

| | | | | |
|---|---|---|---|---|
| 5,059,193 | A * | 10/1991 | Kuslich | A61F 2/4455 606/279 |
| 2009/0099610 | A1* | 4/2009 | Johnson | A61B 17/844 606/86 R |
| 2011/0004308 | A1* | 1/2011 | Marino | A61B 17/8858 219/121.72 |
| 2013/0090655 | A1* | 4/2013 | Tontz | A61B 17/744 606/64 |
| 2013/0317617 | A1* | 11/2013 | Mayer | A61F 2/442 623/17.16 |
| 2020/0038070 | A1* | 2/2020 | Suddaby | A61F 2/4405 |

* cited by examiner

*Primary Examiner* — Marcela I. Shirsat
(74) *Attorney, Agent, or Firm* — Li & Cai Intellectual Property Office

(57) ABSTRACT

A surgical expandable implant includes a bolt, a movable member, and a support body. The bolt has a bolt body and a fixing member. The movable member is configured to be slidably sleeved on the bolt body. The support body has a first end configured to extend through the fixing member and a second end configured to extend through the movable member. The movable member is configured to slide along the length of the bolt body so as to move the support body from an initial shape to a deformed shape.

20 Claims, 10 Drawing Sheets

Fig. 4c
Fig. 4a
Fig. 4d
Fig. 4b

SURGICAL EXPANDABLE IMPLANT

BACKGROUND

A vertebrae collapse may occur due to a variety of causes, e.g., osteoporosis. Its treatment includes implanting and expanding a conventional surgical expandable implant in an osteoporotic spine to reduce compression of a bone thereof. Thereafter, a synthetic material, e.g., bone cement, is injected into the bone and allows it to harden to provide support thereto.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIGS. 4a-4d are schematic front views illustrating movable members of the surgical expandable implant of FIG. 1 according to some embodiments of the present disclosure.

DETAILED DESCRIPTION

Detailed descriptions of the present disclosure are illustrated below in conjunction with the accompanying drawings. However, it is to be understood that the descriptions and the accompanying drawings disclosed herein are merely illustrative and exemplary and not intended to limit the scope of the present disclosure.

Figure 1:
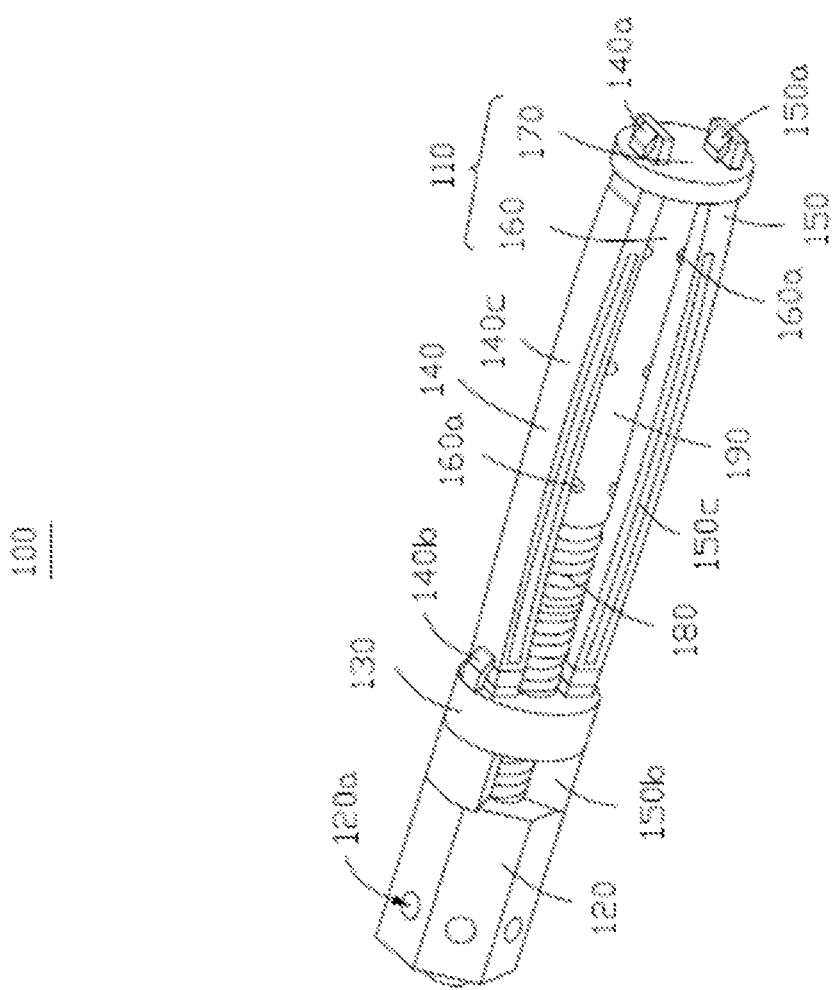
FIG. 1 is a schematic perspective view illustrating a surgical expandable implant according to some embodiments of the present disclosure.

FIG. 1 is a schematic perspective view illustrating a surgical expandable implant 100 according to some embodiments of the present disclosure. As illustrated in FIG. 1, the surgical expandable implant 100 includes a bolt 110, a pushing member 120, a movable member 130, a first support body 140, and a second support body 150. The bolt 110 includes a bolt body 160 and a fixing member 170 that has a larger width than the bolt body 160. In this exemplary embodiment, the fixing member 170 is integral with the bolt body 160. In other words, the bolt body 160 and the fixing member 170 are formed into one piece.

The bolt body 160 has a threaded end portion 180 and an unthreaded end portion 190 between the threaded end portion 180 and the fixing member 170. The bolt body 160 is tubular, defines a bolt channel therein, and is formed with a plurality of bolt holes 160a, each of which extends through a sidewall thereof and is in fluid communication with the bolt channel.

In this exemplary embodiment, the bolt holes 160a are arranged along the threaded and unthreaded end portions 180, 190 of the bolt body 160. In some embodiments, the bolt holes 160a are arranged along the threaded end portion 180. In such some embodiments, the unthreaded end portion 190 is free of bolt holes. In other embodiments, the bolt holes 160a are arranged along the unthreaded end portion 190. In such other embodiments, the threaded end portion 180 is free of bolt holes.

At least one of the bolt 110, the pushing member 120, the movable member 130, and the first and second support bodies 140, 150 is made from a medical grade material, such as titanium, stainless steel, any suitable medical grade material, or a combination thereof. One of the bolt 110, the pushing member 120, the movable member 130, and the first and second support bodies 140, 150 may be made from a different medical grade material than the other of the bolt 110, the pushing member 120, the movable member 130, and the first and second support bodies 140, 150.

The pushing member 120 is threadedly connected to the threaded end portion 180 of the bolt body 160. In certain embodiments, the pushing member 120 is in a form of a nut that has an inner thread. In such certain embodiments, the pushing member 120 has a polygonal cross-section, e.g., hexagonal. It should be understood that, after reading this disclosure, other shapes are contemplated as being within the scope of the present disclosure including, e.g., square, rectangular, or other suitable polygonal shapes.

The movable member 130 is slidably sleeved on the bolt body 160, is disposed between the pushing member 120 and the fixing member 170, and is slidable along the length of the bolt body 160. The first support body 140 includes opposite ends and a deformable member 140c between the opposite ends thereof and is movable from an initial shape to a deformed shape, as will be described in detail further below.

In this exemplary embodiment, the first support body 140 is connected to the fixing member 170 through a first coupling structure 140a. In certain embodiments, the first support body 140 is detachably connected to the fixing member 170 through the first coupling structure 140a. That is, in such certain embodiments, the first support body 140 and the fixing member 170 may be disconnected from each other without damaging the first support body 140 and/or the fixing member 170.

The first support body 140 is further connected to the movable member 130 through a second coupling structure 140b. In certain embodiments, the first support body 140 is detachably connected to the movable member 130 through the second coupling structure 140*b*. That is, in such certain embodiments, the first support body 140 and the movable member 130 may be disconnected from each other without damaging the first support body 140 and/or the movable member 130.

The second support body 150 includes opposite ends and a deformable member 150*c* between the opposite ends thereof and is movable from an initial shape to a deformed shaped, as will be described in detail further below.

The second support body 150 is connected to the fixing member 170 through a first coupling structure 150*a*. In certain embodiments, the second support body 150 is detachably connected to the fixing member 170 through the first coupling structure 150*a*. That is, in such certain embodiments, the second support body 150 and the fixing member 170 may be disconnected from each other without damaging the second support body 150 and/or the fixing member 170.

The second support body 150 is further connected to the movable member 130 through a second coupling structure 150*b*. In certain embodiments, the second support body 150 is detachably connected to the movable member 130 through the second coupling structure 150*b*. That is, in such certain embodiments, the second support body 150 and the movable member 130 may be disconnected from each other without damaging the second support body 150 and/or the movable member 130.

Figure 2:
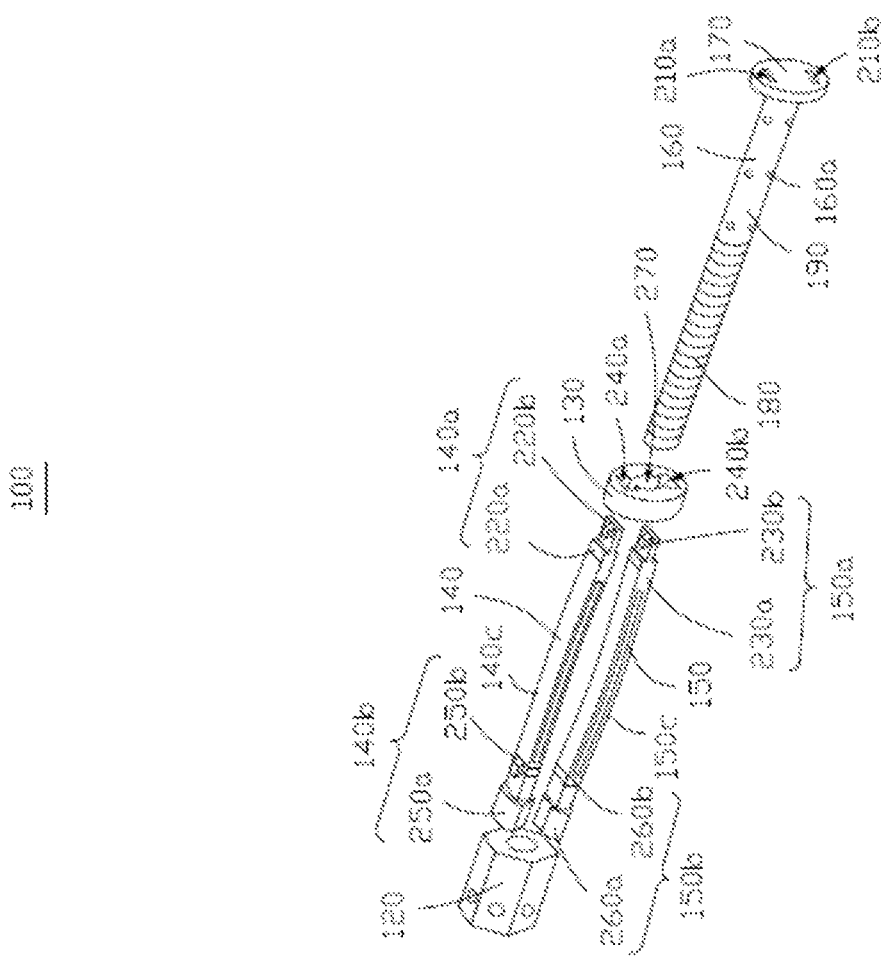
FIG. 2 is a schematic exploded view illustrating the surgical expandable implant of FIG. 1 according to some embodiments of the present disclosure.

FIG. 2 is a schematic exploded view illustrating the surgical expandable implant 100 according to some embodiments of the present disclosure. As illustrated in FIG. 2, the first coupling structure 140*a* includes a coupling hole 210*a* and first and second protruding members 220*a*, 220*b*. The fixing member 170 is formed with the coupling hole 210*a* of the first coupling structure 140*a* therethrough. One of the ends of the first support body 140 is configured to extend through the coupling hole 210*a* in the fixing member 170 such that the fixing member 170 is between the first and second protruding members 220*a*, 220*b* of the first coupling structure 140*a*, whereby the first support body 140 is connected to the fixing member 170. In some embodiments, the second protruding member 220*b* may have a shape of an arrow. In other embodiments, the second protruding member 220*b* may have any other shapes so long as its intended function is achieved.

It should be understood that, after reading this disclosure, other configurations of the first coupling structure 140*a* are contemplated as being within the scope of the present disclosure so long as the first support body 140 can be connected or detachably connected to the fixing member 170.

As further illustrated in FIG. 2, the second coupling structure 140*b* includes a coupling hole 240*a* and first and second protruding members 250*a*, 250*b*. The movable member 130 is formed with the coupling hole 240*a* of the second coupling structure 140*b* therethrough. The other of the ends of first support body 140 is configured to extend through the coupling hole 240*a* in the movable member 130 such that the movable member 130 is between the first and second protruding members 250*a*, 250*b* of the second coupling structure 140*b*, whereby the first support body 140 is connected to the movable member 130. In some embodiments, the second protruding member 250*b* may have a shape of an arrow. In other embodiments, the second protruding member 250*b* may have any other shapes so long as its intended function is achieved.

It should be understood that, after reading this disclosure, other configurations of the second coupling structure 140*b* are contemplated as being within the scope of the present disclosure so long as the first support body 140 can be connected or detachably connected to the movable member 130.

As further illustrated in FIG. 2, the first coupling structure 150*a* includes a coupling hole 210*b* and first and second protruding members 230*a*, 230*b*. The fixing member 170 is formed with the coupling hole 210*b* of the first coupling structure 150*a* therethrough. In this exemplary embodiment, the coupling holes 210*a*, 210*b* are diametrically opposed to each other. One of the ends of the second support body 150 is configured to extend through the coupling hole 210*b* in the fixing member 170 such that the fixing member 170 is between the first and second protruding members 230*a*, 230*b* of the first coupling structure 150*a*, whereby the second support body 150 is connected to the fixing member 170. In some embodiments, the second protruding member 230*b* may have a shape of an arrow. In other embodiments, the second protruding member 230*b* may have any other shapes so long as its intended function is achieved.

The construction as such of the first coupling structure 140*a*, 150*a* permits stable connection between the support body 140, the movable member 130, and the bolt 110.

It should be understood that, after reading this disclosure, other configurations of the first coupling structure 150*a* are contemplated as being within the scope of the present disclosure so long as the second support body 150 can be connected or detachably connected to the fixing member 170.

As further illustrated in FIG. 2, the second coupling structure 150*b* includes a coupling hole 240*b* and first and second protruding members 260*a*, 260*b*. The movable member 130 is formed with the coupling hole 240*b* of the second coupling structure 150*b* therethrough. In this exemplary embodiment, the coupling holes 240*a*, 240*b* are diametrically opposed to each other. The other of the ends of the second support body 150 is configured to extend through the second coupling hole 240*b* in the movable member 130 such that the movable member 130 is between the first and second protruding members 260*a*, 260*b* of the second coupling structure 150*b*, whereby the second support body 150 is connected to the movable member 130. In some embodiments, the second protruding member 260*b* may have a shape of an arrow. In other embodiments, the second protruding member 260*b* may have any other shapes so long as its intended function is achieved.

It should be understood that, after reading this disclosure, other configurations of the second coupling structure 150*b* are contemplated as being within the scope of the present disclosure so long as the second support body 150 can be connected or detachably connected to the movable member 130.

With reference to FIGS. 1 and 2, when it is desired to assemble the surgical expandable implant 100, the first support body 140 is connected to the movable member 130 through the second coupling structure 140*b*, during which the second protruding member 250*b* of the second coupling structure 140*b* and/or the movable member 130 may deform and return back to its/their original shape. Then, the second support body 150 is connected to the movable member 130 through the second coupling structure 150*b*, during which the second protruding member 260*b* of the second coupling structure 150*b* and/or the movable member 130 may deform and return back to its/their original shape. Subsequently, the movable member 130 is sleeved on the bolt body 160 such that the bolt body extends through a through hole 270 in movable member 130.

Next, the first support body 140 is connected to the fixing member 170 through the first coupling structure 140a, during which the second protruding member 220b of the first coupling structure 140a and/or the fixing member 170 may deform and return back to its/their original shape. Thereafter, the second support body 150 is connected to the fixing member 170 through the first coupling structure 150a, during which the second protruding member 230b of the first coupling structure 150a and/or the fixing member 170 may deform and return back to its/their original shape. Finally, the pushing member 120 is threadedly connected to the threaded end portion 180 of the bolt body 160.

FIGS. 3a-3d are schematic perspective and side views illustrating the surgical expandable implant 100 in states of use according to some embodiments of the present disclosure. In this exemplary embodiment, the surgical expandable implant 100 further includes a tool 310 configured to move the deformable members 140c, 150c from an initial shape, as shown, e.g., in FIG. 3a, to a deformed shape, as shown, e.g., in FIG. 3b.

It is noted herein that the lengths of the threaded and unthreaded end portions 180, 190 of the bolt body 160 are predetermined. The position of the movable member 130 relative to the fixing member 170 determines the degree of deformation of the deformable members 140c, 150c. The junction of the threaded and unthreaded end portions 180, 190 restricts the movement of the movable member 130 beyond the threaded end portion 180 and therefore determines the maximum degree of deformation of the deformable members 140c, 150c.

Figure 3B:
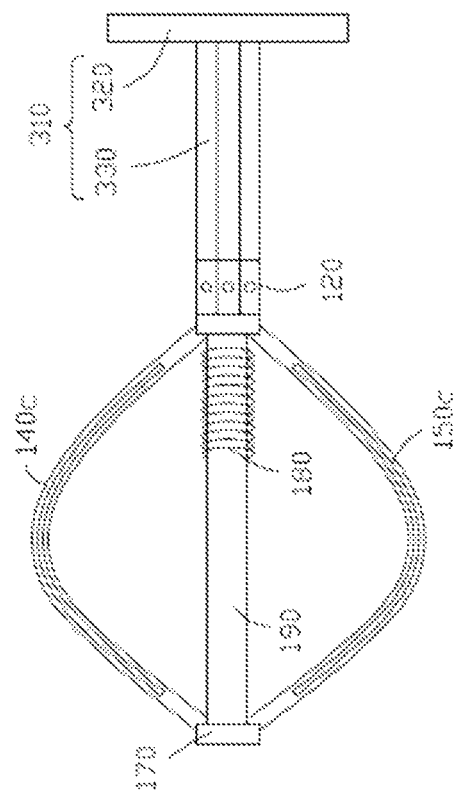
FIG. 3b is a schematic side view illustrating the surgical expandable implant of FIG. 1 in a state of use according to some embodiments of the present disclosure.
Figure 3A:
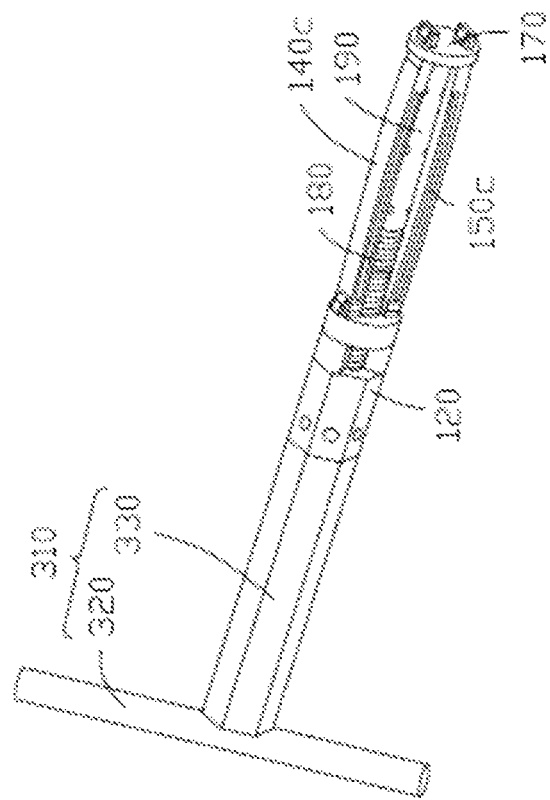
FIG. 3a is a schematic perspective view illustrating the surgical expandable implant of FIG. 1 in a state of use according to some embodiments of the present disclosure.

In this exemplary embodiment, as illustrated in FIG. 3a, the tool 310 has a generally "T" shape and includes a first tool portion 320 and a second tool portion 330 having an end connected to a middle of the first tool portion 320. The middle of the first tool portion 320 is formed with a tool hole therethrough.

The second tool portion 330 of the tool 310 is tubular and defines a tool channel therein in fluid communication with the tool hole in the first tool portion 320. In this exemplary embodiment, the second tool portion 330 has a polygonal cross-section, e.g., hexagonal. It should be understood that, after reading this disclosure, other shapes are contemplated as being within the scope of the present disclosure including, for example, square, rectangular, or other polygonal shapes.

In use, the tool 310 is inserted into a recess in the pushing member 120, as illustrated in FIG. 3a. Then, the surgical expandable implant 100 is implanted into an object, e.g., a bone, a vertebrae, a vertebral disc, and the like, using the tool 310. It is noted that the recess in the pushing member 120 has a cross-section that corresponds to the cross-section of the second tool portion 330 of the tool 310. Next, the second tool portion 330 of the tool 310 is rotated, e.g., in a clockwise direction, using the first tool portion 320 of the tool 310 such that the pushing member 120 moves along the length of the bolt body 160 toward the fixing member 170, during which the pushing member 120 pushes the movable member 130 along the length of the bolt body 160 toward the fixing member 170. As a result, each of the deformable members 140c, 150c moves from an initial shape, as shown, e.g., in FIG. 3a, to a deformed shape, as shown, e.g., in FIG. 3b. At this time, the threaded end portion 180 of the bolt body 160 may extend into the tool channel of the second tool portion 330 of the tool 310.

The second tool portion 330 of the tool 310 may be rotated, e.g., in a counterclockwise direction, using the first tool portion 320 of the tool 310 such that the pushing member 120 moves along the length of the bolt body 160 away from the fixing member 170, during which the movable member 130 moves along the length of the bolt body 160 away from the fixing member 170. As a result, each of the deformable members 140c, 150c moves from the deformed shape toward the initial shape.

Figure 3D:
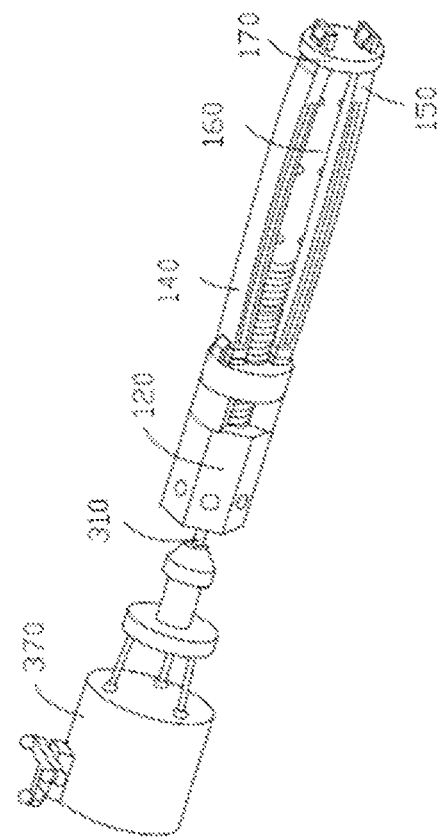
FIG. 3d is a schematic perspective view illustrating the surgical expandable implant of FIG. 1 in a state of use according to some embodiments of the present disclosure.
Figure 3C:
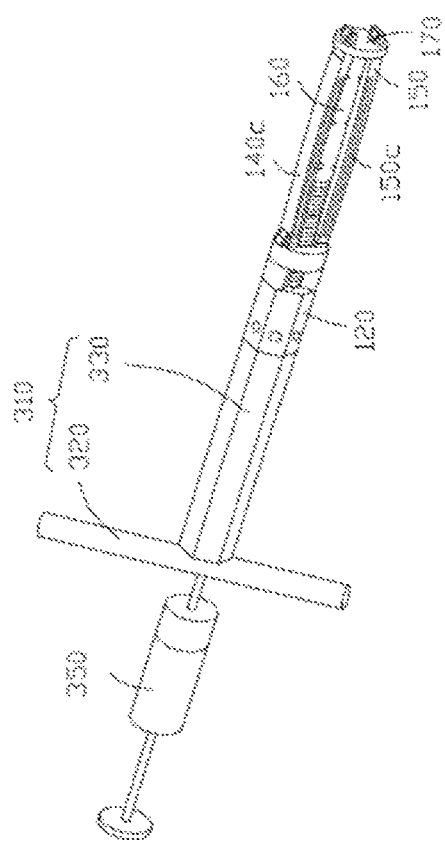
FIG. 3c is a schematic perspective view illustrating the surgical expandable implant of FIG. 1 in a state of use according to some embodiments of the present disclosure.

Next, as illustrated in FIG. 3c, a synthetic material, e.g., bone cement, may be injected into the object through the tool hole and the tool channel in tool 310 and the bolt channel and the bolt holes 160a in the bolt body 160 using a surgical instrument 350. Thereafter, the tool 310 is removed from the pushing member 120, thereby detaching the tool 310 from the surgical expandable implant 100 and leaving the surgical expandable implant 100 in the object.

Although the tool 310 of the surgical expandable implant 100 is exemplified having a "T" shape, in an alternative embodiment, the tool 310 of the surgical expandable implant 100 may have other shapes. For example, in some embodiments, the tool 310 of the surgical expandable implant 100 has an "L" shape. In other embodiments, the tool 310 of the surgical expandable implant 100 has a rod shape. In such other embodiments, as illustrated in FIG. 3d, an end of the tool 310 may be clamped and rotated by a surgical instrument 370.

In this exemplary embodiment, the surgical expandable implant 100 further includes a latch unit that facilitates connection of the pushing member 120 and the tool 310 therebetween. For example, the latch unit may include a plurality of latch grooves formed in an end of the second tool portion 330 of the tool 310, a plurality of latch holes, e.g., latch holes 120a of FIG. 1, formed in a sidewall of the pushing member 120, and a plurality of latch balls, each of which is disposed in a respective one of the latch holes 120a and is configured to engage a respective one of the latch grooves in the second tool portion 330 of the tool 310. In an alternative embodiment, the latch grooves are provided on the pushing member 120 and the latch holes 120a and the latch balls are provided on the second tool portion 330 of the tool 310.

FIGS. 4a-4d are schematic front views illustrating movable members of the surgical expandable implant 100 according to some embodiments of the present disclosure. Although the movable member 130 of the surgical expandable implant 100 is exemplified with a pair of coupling holes 240a, 240b, as illustrated in FIG. 4a, it should be apparent that, after reading this disclosure, the number of coupling holes of the surgical expandable implant 100 may be decreased or increased as required. For example, in some embodiments, as illustrated in FIG. 4b, the movable member 420 may be formed with four coupling holes 420a-420d therethrough. In other embodiments, as illustrated in FIG. 4c, the movable member 410 may be formed with three coupling holes 410a-410c therethrough. In certain embodiments, as illustrated in FIG. 4d, the movable member 430 may be formed with a single coupling hole 430a therethrough.

Figure 5A:
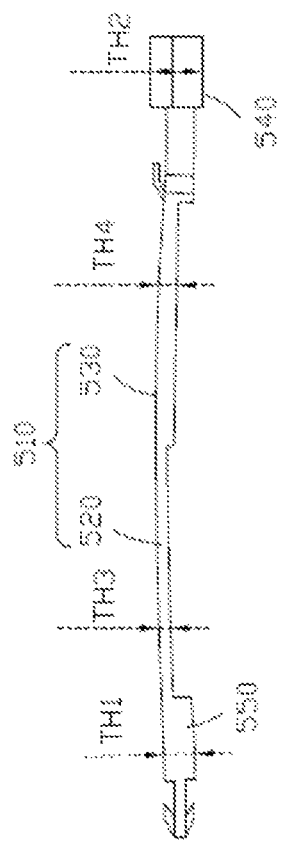
FIGS. 5a-5d are schematic side views illustrating support bodies of the surgical expandable implant of FIG. 1 according to some embodiments of the present disclosure.
Figure 5B:
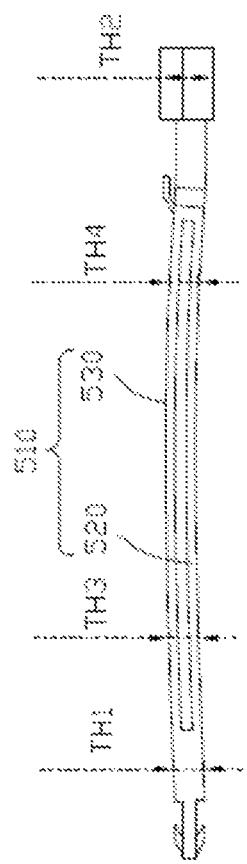
Figure 5C:
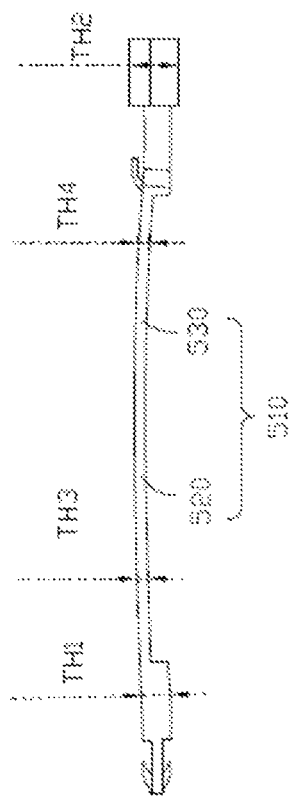
Figure 5D:
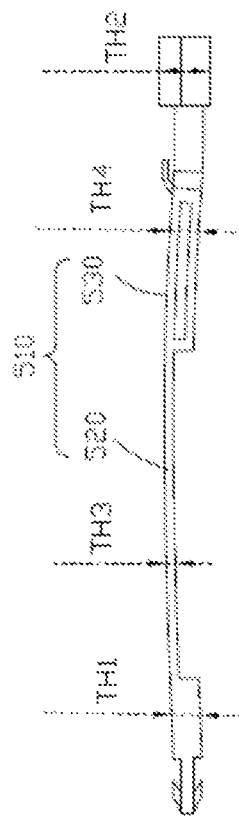
Figure 6C:
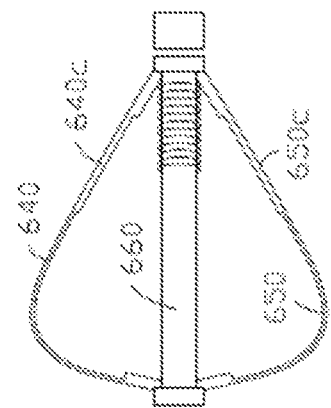
FIGS. 6a-6d are schematic side views illustrating states where support bodies of the surgical expandable implant of FIG. 1 in deformed shapes according to some embodiments of the present disclosure.
Figure 6D:
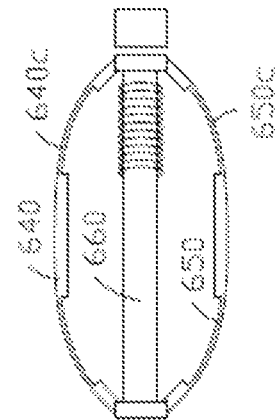
Figure 6A:
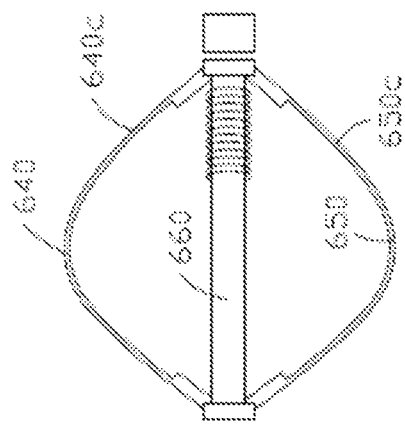
Figure 6B:
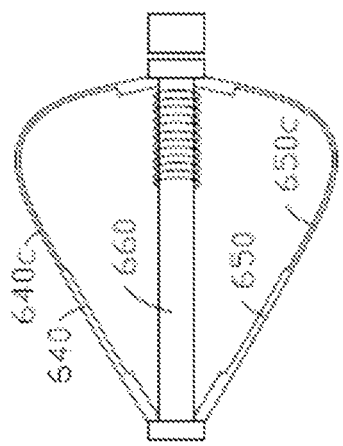
Figure 7C:
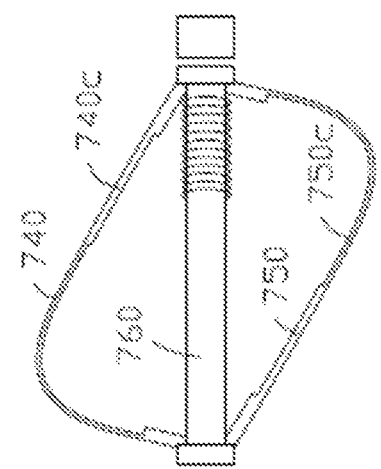
FIGS. 7a-7d are schematic side views illustrating states where support bodies of the surgical expandable implant of FIG. 1 in deformed shapes according to some embodiments of the present disclosure.
Figure 7D:
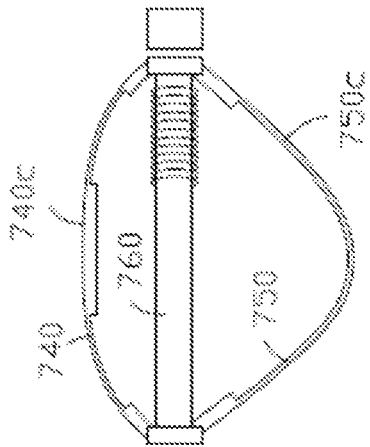
Figure 7A:
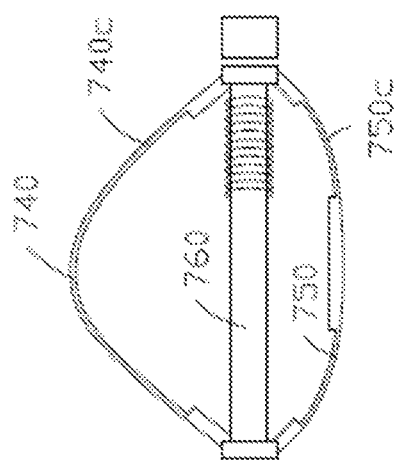
Figure 7B:
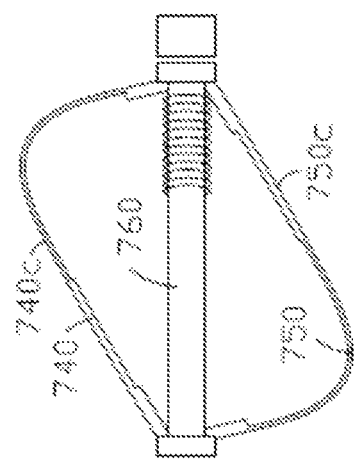

FIGS. 5a-5d are schematic side views illustrating support bodies of the surgical expandable implant 100 according to some embodiments of the present disclosure. In this exemplary embodiment, at least one of the support bodies, e.g., support bodies 140, 150, of the surgical expandable implant 100 has a non-uniform thickness. For example, as illustrated in FIGS. 5a and 5d, the support body 510 includes a first end portion 520 that has a thickness (TH3) less than a thickness (TH4) of a second end portion 530 thereof. In some embodiments, as illustrated in FIG. 5a, the second end portion 530 of the support body 510 is solid. In other embodiments, as illustrated in FIG. 5d, the second end portion 530 of the support body 510 is hollow. In an alternative embodiment, the first end portion 520 of the support body 510 has a different elastic modulus than the second end portion 530 of the support body 510.

In certain embodiments, at least one of the support bodies, e.g., support bodies 140, 150, of the surgical expandable implant 100 has a thickness that gradually increases or decreases from an end to the other end thereof.

In various embodiments, at least one of the support bodies, e.g., support bodies 140, 150, of the surgical expandable implant 100 has a substantially uniform thickness. For example, as illustrated in FIGS. 5b and 5c, a thickness (TH3) of the first end portion 520 of the support body is substantially the same as a thickness (TH4) of the second end portion 530 of the support body 510. In some embodiments, as illustrated in FIG. 5c, the first and second end portions 520, 530 of the support body 510 are solid. In other embodiments, as illustrated in FIG. 5b, the first and second end portions 520, 530 of the support body 510 are hollow.

It is noted that, as shown in FIGS. 5a-5d, the protruding member 540 of the coupling structure, e.g., second coupling structures 140b, 150b of FIG. 2, has a thickness (TH2) greater than a thickness (TH1) of the protruding member 550 of the coupling structure, e.g., first coupling structures 140a, 150a of FIG. 2.

FIGS. 6a-6d and 7a-7d are schematic side views illustrating states where the surgical expandable implant 100 in deformed shapes according to some embodiments of the present disclosure. In some embodiments, the surgical expandable implant 100 may be assembled with first and second support bodies 640, 650 that are of the same configurations as each other. For example, the first and second support bodies 640, 650 may have the configuration of one of the support bodies 510 shown in FIGS. 5a-5d. As such, when the first and second bodies 640, 650 are move from an initial shape to a deformed shape, the deformable members 640c, 650c may have shapes or curvatures, that are substantially symmetrical with respect to the bolt body 660, as illustrated in FIGS. 6a-6d.

In other embodiments, the surgical expandable implant 100 may be assembled with first and second support bodies 740, 750 that are of different configurations from each other. For example, the first and second support bodies 740, 750 may have the configuration of one of the support bodies 510 shown in FIGS. 5a-5d. As such, when the first and second support bodies 740, 750 are moved from an initial shape to a deformed shape, the deformable members 740c, 750c may have different shapes or curvatures, as illustrated in FIGS. 7a-7d.

Figure 8B:
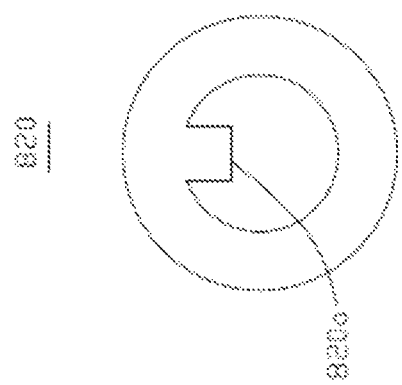
FIG. 8b is a schematic cross-sectional view illustrating a pushing member of another surgical expandable implant according to some embodiments of the present disclosure.
Figure 8A:
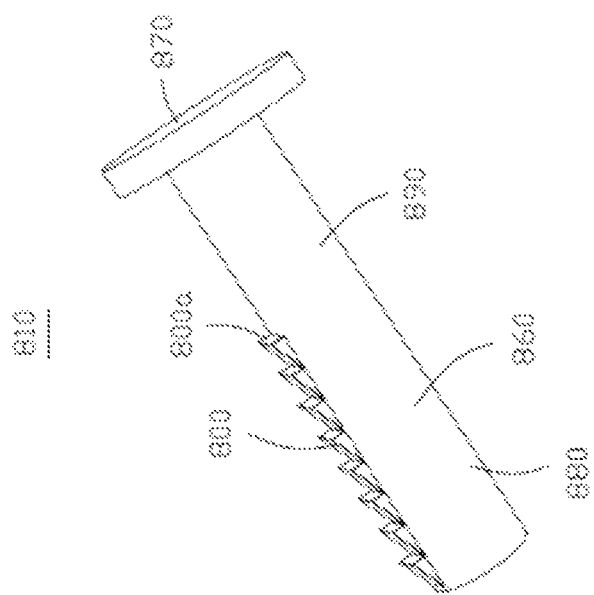
FIG. 8a is a schematic perspective view illustrating a bolt of another surgical expandable implant according to some embodiments of the present disclosure.

FIGS. 8a and 8b are respectively schematic perspective and cross-sectional views of a bolt and a pushing member of another surgical expandable implant according to some embodiments of the present disclosure. The surgical expandable implant of this embodiment differs from the surgical expandable implant 100 in that, as illustrated in FIG. 8a, the bolt body 860 of the bolt 810 has a first end portion 880 and a second end portion 890 between the first end portion 880 and the fixing member 870. The first end portion 880 of the bolt body 860 is formed with a plurality of bolt teeth 800, each of which has an edge 800a substantially at right angle to the length of the bolt body 860. Further, instead of an inner thread, as illustrated in FIG. 8b, the pushing member 820 is formed with an inner protrusion 820a therein configured to engage the edge 800a of one of the bolt teeth 800. The second end portion 890 of the bolt body 860 is free of bolt teeth.

In an embodiment, a surgical expandable implant comprises a bolt, a movable member, and a support body. The bolt has a bolt body and a fixing member. The movable member is configured to be slidably sleeved on the bolt body. The support body has a first end configured to extend through the fixing member and a second end configured to extend through the movable member. The movable member is configured to slide along the length of the bolt body so as to move the support body from an initial shape to a deformed shape.

In another embodiment, a surgical expandable implant comprises a bolt, a movable member, a support body, and a coupling structure. The bolt has a bolt body and a fixing member. The movable member is configured to be slidably sleeved on the bolt body. The support body is configured to be coupled between the fixing member and the movable member. The movable member is configured to slide along the length of the bolt body so as to move the support body from an initial shape to a deformed shape. The coupling structure includes a coupling hole in the movable member and a pair of protruding members on an end of the support body. When the end of the support body extends through the coupling hole, the movable member is between the protruding members.

In another embodiment, a surgical expandable implant comprises a bolt, a movable member, a support body, and a coupling structure. The bolt includes a fixing member and a bolt body. The movable member is configured to be slidably sleeved on the bolt body. The support body is configured to be coupled between the fixing member and the movable member. The movable member is configured to slide along the length of the bolt body so as to move the support body from an initial shape to a deformed shape. The coupling structure includes a coupling hole in the fixing member and a pair of protruding members on an end of the support body. When the end of the support body extends through the coupling hole, the fixing member is between the protruding members.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A surgical expandable implant comprising:
a bolt having a bolt body and a fixing member;
a movable member configured to be slidably sleeved on the bolt body; and
a support body detachably assembled between the movable member and the fixing member and having a first end configured to extend through the fixing member and a second end configured to extend through the movable member;
a first coupling structure located at the first end of the support body, wherein the first coupling structure includes first and second protruding members connected to each other, and the second protruding member of the first coupling structure is configured to pass through the fixing member, such that the fixing member is located between the first protruding member of the first coupling structure and the second protruding member of the first coupling structure, and the fixing member abuts against the first protruding member of the first coupling structure, a thickness of the second protruding member of the first coupling structure gradually decreases along a direction away from the first protruding member of the first coupling structure; and a second coupling structure located at the second end of the support body, wherein the second coupling structure includes first and second protruding members connected to each other, and the second protruding member of the second coupling member is configured to pass through the movable member, such that the movable member is located between the first protruding member of the second coupling structure and the second protruding member of the second coupling structure, and the movable member abuts against the first protruding member of the second coupling structure, a thickness of the second protruding member of the second coupling structure gradually decreases along a direction away from the first protruding member of the second coupling structure;

wherein the movable member is configured to slide along the length of the bolt body so as to move the support body from an initial shape to a deformed shape.

2. The surgical expandable implant of claim 1, further comprising a pushing member configured to be sleeved on the bolt body and to push the movable member to slide along the length of the bolt body.

3. The surgical expandable implant of claim 1, wherein the movable member includes a coupling hole, and the second protruding member of the second coupling structure is configured to extend through the coupling hole.

4. The surgical expandable implant of claim 1, wherein the fixing member includes
a coupling hole, and the second protruding member of the first coupling structure is configured to extend through the coupling hole.

5. The surgical expandable implant of claim 1, wherein the support body has a first end portion and a second end portion that has a larger thickness than the first end portion.

6. The surgical expandable implant of claim 1,
wherein the second coupling structure has a larger thickness than the first coupling structure.

7. The surgical expandable implant of claim 1, further comprising a pushing member configured to be threadedly coupled to the bolt body and to push the movable member along the length of the bolt body.

8. The surgical expandable implant of claim 1, wherein the bolt body is tubular, defines a bolt channel therein, and is formed with a plurality of bolt holes through a sidewall thereof and in fluid communication with the bolt channel.

9. The surgical expandable implant of claim 8, further comprising:
a pushing member configured to be sleeved on the bolt body and to push the movable member along the length of the bolt body; and
a tool configured to move the pushing member along the length of the bolt body.

10. The surgical expandable implant of claim 9, wherein the tool is tubular and is configured to be in fluid communication with the bolt body.

11. The surgical expandable implant of claim 1, wherein the support body is hollow.

12. A surgical expandable implant comprising:
a bolt having a bolt body and a fixing member;
a movable member configured to be slidably sleeved on the bolt body and including a coupling hole;
a support body detachably assembled between the fixing member and the movable member and having a first end configured to extend through the fixing member and a second end configured to extend through the movable member, wherein the movable member is configured to slide along the length of the bolt body so as to move the support body from an initial shape to a deformed shape; and
a coupling structure located at the second end of the support body and configured to connect the support body to the movable member, wherein the coupling structure includes first and second protruding members connected to each other, the second protruding member is configured to pass through the movable member by the coupling hole, such that the movable member is located between the first protruding member and the second protruding member, and the movable member abuts against the first protruding member, a thickness of the second protruding member gradually decreases along a direction away from the first protruding member.

13. The surgical expandable implant of claim 12, further comprising a pushing member configured to be sleeved on the bolt body and to push the movable member along the length of the bolt body.

14. The surgical expandable implant of claim 12, wherein the bolt body has a threaded end portion and an unthreaded end portion between the fixing member and the threaded end portion.

15. The surgical expandable implant of claim 12, further comprising a pushing member configured to be threadedly coupled to the bolt body and to push the movable member along the length of the bolt body.

16. The surgical expandable implant of claim 12, wherein the bolt body is tubular and defines a channel therein.

17. A surgical expandable implant comprising:
a bolt including a fixing member and a bolt body, the fixing member having a coupling hole;
a movable member configured to be slidably sleeved on the bolt body;
a support body detachably assembled between the fixing member and the movable member and having a first end configured to extend through the fixing member and a second end configured to extend through the movable member, wherein the movable member is configured to slide along the length of the bolt body so as to move the support body from an initial shape to a deformed shape; and
a coupling structure located at the first end of the support body and configured to connect the support body to the fixing member, wherein the coupling structure includes first and second protruding members connected to each other, the second protruding member is configured to pass through the coupling hole, such that the fixing member is located between the first protruding member and the second protruding member, and the fixing member abuts against the first protruding member, a thickness of the second protruding member gradually decreases along a direction away from the first protruding member.

18. The surgical expandable implant of claim 17, wherein the bolt body is formed with a plurality of bolt teeth, each of which has an edge at right angle to the length of the bolt body.

19. The surgical expandable implant of claim 18, wherein the bolt body has a first end portion formed with the bolt teeth and a second end portion between the first end portion and the fixing member and free of bolt teeth.

20. The surgical expandable implant of claim 18, further comprising a pushing member configured to be sleeved on the bolt body and to push the movable member to slide along the length of the bolt body, wherein the pushing member is formed with an inner protrusion configured to engage the edge of one of the bolt teeth.

* * * * *